United States Patent [19]

Wilkes et al.

[11] Patent Number: 4,919,765
[45] Date of Patent: Apr. 24, 1990

[54] PROCESS FOR THE PURIFICATION OF TETRAHYDROFURAN

[75] Inventors: Peter R. Wilkes, Rickmansworth; John Scarlett, Spennymoor; George E. Harrison, Billericay, all of England

[73] Assignee: Davy McKee (London) Limited, London, England

[21] Appl. No.: 222,727

[22] Filed: Jul. 22, 1988

[30] Foreign Application Priority Data

Jul. 29, 1987 [GB] United Kingdom ............... 8717993

[51] Int. Cl.⁵ ............................................. B01D 3/34
[52] U.S. Cl. .................................. 203/64; 203/4; 203/14; 203/74; 203/77; 203/80; 203/82; 203/84; 203/DIG. 9; 203/DIG. 13; 549/295; 549/429; 549/509; 568/868; 568/869
[58] Field of Search .................. 203/4, 14, 64, 80, 82, 203/74, 84, 77, DIG. 9, DIG. 13; 549/429, 295, 509; 568/868, 869

[56] References Cited

U.S. PATENT DOCUMENTS

| | | | |
|---|---|---|---|
| 2,636,050 | 4/1953 | Hoaglin et al. | 560/248 |
| 3,692,859 | 9/1972 | Cottle | 549/429 |
| 4,032,458 | 6/1977 | Cooley et al. | 568/868 |
| 4,032,583 | 6/1977 | Arganbright et al. | 568/868 |
| 4,048,196 | 9/1977 | Broecker et al. | 549/508 |
| 4,093,633 | 6/1978 | Tanabe et al. | 549/509 |
| 4,175,009 | 11/1979 | Copelin | 203/96 |
| 4,332,645 | 6/1982 | Müller et al. | 203/75 |
| 4,665,205 | 5/1987 | Yamada et al. | 549/509 |
| 4,767,869 | 8/1988 | Harrison et al. | 549/295 |

FOREIGN PATENT DOCUMENTS

| | | |
|---|---|---|
| 0143634 | 11/1984 | European Pat. Off. . |
| 0255400 | 7/1987 | European Pat. Off. . |
| 0255401 | 7/1987 | European Pat. Off. . |
| 0142298 | 6/1980 | German Democratic Rep. . |
| 0237056 | 7/1986 | German Democratic Rep. . |
| 0020010 | 6/1972 | Japan ............... 549/429 |
| 56-108722 | 1/1980 | Japan . |
| 8603189 | 6/1986 | PCT Int'l Appl. . |
| 8607358 | 12/1986 | PCT Int'l Appl. . |
| 8800937 | 2/1988 | PCT Int'l Appl. . |
| 0549464 | 4/1977 | U.S.S.R. ............. 549/429 |
| 1025709 | 5/1979 | U.S.S.R. . |
| 0968034 | 7/1981 | U.S.S.R. . |
| 2175894 | 12/1986 | United Kingdom ....... 549/295 |
| 2193207 | 2/1988 | United Kingdom . |

Primary Examiner—Virginia Manoharan
Attorney, Agent, or Firm—Bernard, Rothwell & Brown

[57] ABSTRACT

Tetrahydrofuran is recovered by a two stage distillation procedure from a crude hydrogenation product resulting from vapor phase hydrogenation of diethyl maleate and containing water, ethanol and a minor amount of n-butanol, and possibly also dissolved hydrogen, in addition to butane-1,4-diol, gamma-butyrolactone and "heavies" such as diethyl ethoxysuccinate. In the first distillation stage, conveniently operated substantially at atmospheric pressure, ethanol, water, and tetrahydrofuran are recovered as overhead product, are condensed to separate the condensible components from a hydrogen stream which can be vented, and then redistilled in the presence of a molar excess of a hydroxylic solvent containing at least two hydroxyl groups, such as butane-1,4-diol, in a second distillation zone. Pure tetrahydrofuran is recovered as overhead product from the second distillation zone, while the bottom product therefrom is stripped in a third distillation zone of tetrahydrofuran, ethanol and water which are recycled to the first distillation zone and the stripped bottom product is recycled to the second distillation zone.

18 Claims, 1 Drawing Sheet

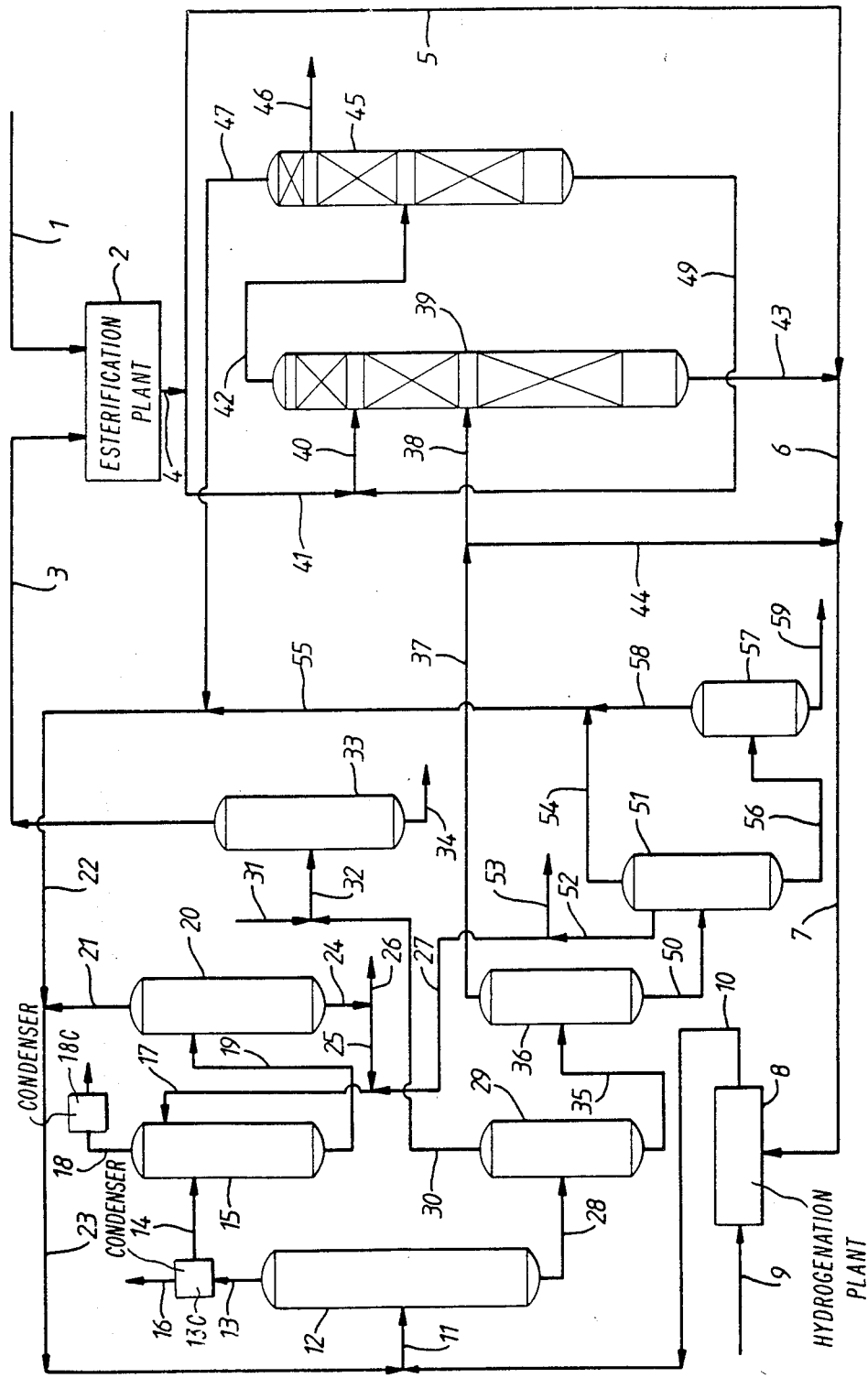

PROCESS FOR THE PURIFICATION OF TETRAHYDROFURAN

This invention relates to a process for the production of tetrahydrofuran. More particularly it relates to a continuous process for the separation of tetrahydrofuran from a crude reaction product containing, in addition to tetrahydrofuran, also minor amounts of ethanol, water, n-butanol and significant amounts of high boiling materials including butane-1,4-diol and gamma-butyrolactone.

Production of tetrahydrofuran by hydrogenation of butyl maleate or succinate in the presence of a catalyst containing cobalt, molybdenum and aluminium oxides is described in SU-A-968034.

In EP-A-0143634 there is described a process for the production of butane-1,4-diol in which vapor phase hydrogenation of an ester of a $C_4$ dicarboxylic acid, for example an ester of maleic acid, such as diethyl maleate, is carried out in two reactors in series, using a copper chromite hydrogenation catalyst. Further teaching regarding this process can be found in WO-A-86/03189. A modified process in which the major product is gamma-butyrolactone is described in WO-A-86/07358.

In such processes the reaction conditions can be varied so as to produce different proportions of butane-1,4-diol, of gamma-butyrolactone and of tetrahydrofuran, which is a co-product of the process. If desired, a dehydration section can be included in the plant as taught, for example, by WO-A-86/03189, in order to enhance the yield of tetrahydrofuran. By varying the conditions in the hydrogenation reactors and by use, if necessary, of the dehydration section, the output from the hydrogenation plant can be varied in response to market demand for the three products, i.e. butane-1,4-diol, gamma-butyrolactone, and tetrahydrofuran.

In all cases the hydrogenation product contains, in addition to butane-1,4-diol and gamma-butyrolactone, a number of low boiling materials including tetrahydrofuran, ethanol, water and traces of n-butanol. However, the separation of these low boiling materials with a view to recovering a pure tetrahydrofuran product is problematic as various components of the mixture form azeotropes one with another. In particular, tetrahydrofuran forms azeotropes with water, as well as with ethanol. The azeotrope with water has a boiling point at atmospheric pressure of 64° C., while the azeotrope of tetrahydrofuran and ethanol boils at 65.5° C. at atmospheric pressure. Hence any attempt to separate the low boiling components of the crude reaction product by normal distillative methods results in production of an azeotrope, usually a tetrahydrofuran/water azeotrope, rather than leading to recovery of pure tetrahydrofuran (boiling point 66° C. at 1 bar).

In US-A-4665205 butane-1,4-diol is contacted with a dehydration catalyst, such as 97% aqueous sulphuric acid, to yield a reaction mixture comprising an aqueous 80% by weight tetrahydrofuran solution with a water content of 20% by weight. This is then subjected to extractive distillation using butane-1,4-diol as an extraction solvent at a temperature in the range of from 40° C. to 200° C. and at a pressure of from 0.1 to 9.8 bar (0.1 to 10 kg/cm$^2$). Tetrahydrofuran is recovered as one stream from the extractive distillation column, from which is also recovered a second stream containing water and butane-1,4-diol. Water is stripped from this second stream and the resulting butane-1,4-diol is recycled to the dehydration step.

Extractive distillation with added water is used to separate tetrahydrofuran from one or more aliphatic alcohols, such as ethanol, according to the teachings of US-A-4175009. Use of ethylene glycol or butane-1,4-diol as extractive solvent for the separation by extractive distillation of a methanol/tetrahydrofuran mixture is described in SU-A-1025709. A dilute solution of an alkali in a polyhydric alcohol, such as ethylene glycol or butane-1,4-diol, is used to separate the components of a methanol/tetrahydrofuran azeotrope in the process of DD-A-237056.

In EP-A-0255400 there is described a process for the production of substantially pure gamma-butyrolactone from a feed mixture containing a major molar amount of gamma-butyrolactone and a minor amount of diethyl succinate. Such a feed mixture may result from hydrogenation of diethyl maleate according to the teachings of EP-A-0143634, WO-A-86/03189, and/or WO-A-86/07358. In EP-A-0255400 which was published on Feb. 3, 1988, there is described a process in which the "light ends", i.e. a mixture of tetrahydrofuran, ethanol, water, and n-butanol, are stripped off in a first distillation column which is operated under vacuum at a pressure of 0.27 bar with a head temperature of 48° C. The "light ends" which are recovered overhead are passed to a second distillation column which is operated at 1.2 bar at a head temperature of 58° C. A first tetrahydrofuran/water azeotrope is recovered overhead from this second distillation column which is passed to a third distillation column operated at 7.0 bar with a head temperature of 126° C. Essentially pure tetrahydrofuran is recovered as a bottom product from the third distillation column, whilst the overhead product therefrom is a second tetrahydrofuran/water azeotrope which is markedly richer in water than the first tetrahydrofuran/water azeotrope from the second column. This second azeotrope is recycled to the second column.

This method of recovering tetrahydrofuran requires distillation under three different pressures, i.e. under vacuum (at 0.27 bar), under slightly elevated pressure (at 1.2 bar) and at a moderately elevated pressure (7.0 bar). Distillation of mixtures containing tetrahydrofuran under vacuum is, however, best avoided since there is a risk of formation of explosive peroxides by reaction of air sucked into the system, possibly as a result of an inadvertent leak, with tetrahydrofuran. Moreover, as the crude hydrogenation product contains dissolved hydrogen, there is a risk of venting an explosive mixture of air and hydrogen if a vacuum system is used. Furthermore, the operation of the third distillation column at elevated pressure (at 7 bar) adds to the cost of the plant and of the operating costs therefor.

The present invention seeks to overcome the disadvantages associated with the recovery of tetrahydrofuran described in EP-A-0255400. It further seeks to provide a process in which a vacuum distillation step, with its attendant risk of formation of explosive peroxides, is avoided. Yet again it seeks to provide a process for recovery of pure tetrahydrofuran in which hydrogen dissolved in the crude hydrogenation product can be safely vented. It further seeks to provide a process for recovery of tetrahydrofuran from a crude hydrogenation product obtained by hydrogenation of a dialkyl maleate, such as diethyl maleate, which can be operated at atmospheric pressure.

According to the present invention there is provided a continuous process for the separation of tetrahydrofuran from a crude reaction product containing, in addition to tetrahydrofuran, also ethanol, water, and n-butanol, and significant amounts of high boiling materials including butane-1,4-diol and gamma-butyrolactone, which process comprises:

(a) supplying the crude reaction product to a first distillation zone;
(b) recovering a vaporous first overhead product from the first distillation zone containing tetrahydrofuran, ethanol and water;
(c) redistilling the overhead product from the first distillation zone in a second distillation zone;
(d) supplying to an upper part of the second distillation zone a hydroxylic solvent containing at least two hydroxyl groups;
(e) recovering an overhead product from the second distillation zone consisting essentially of tetrahydrofuran;
(f) recovering a bottom product from a lower part of the second distillation zone comprising hydroxylic solvent, tetrahydrofuran, ethanol and water;
(g) stripping tetrahydrofuran, ethanol and water from the bottom product of step (f) by distillation in a third distillation zone; and
(h) recycling stripped bottom product of step (g) to the second distillation zone.

The crude reaction product may comprise a crude hydrogenation product obtained by vapor phase hydrogenation of an ester of maleic acid, such as diethyl maleate, which has been carried out according to the teachings of EP-A-0143634, WO-A-86/03189 and/or WO-A-86/07358. Such crude hydrogenation products typically contain at least about 10 mol %, up to about 70 mol % or more, of ethanol, at least about 5 mol % each, up to about 20 mol % each or more, of butane-1,4-diol and gamma-butyrolactone, not more than about 10 mol % of tetrahydrofuran, not more than about 15 mol % of water, and not more than about 2 mol % of n-butanol. They may further include a minor amount of diethyl succinate and minor amounts of other by-products, such as diethyl ethoxysuccinate. Typically such minor amounts do not exceed about 5 mol % each.

In a preferred process according to the invention the first distillation zone is operated substantially at atmospheric pressure. Preferably the second distillation zone is operated substantially at atmospheric pressure.

The overhead product from the first distillation zone is advantageously condensed prior to entry to the second distillation zone. In this case the condensate resulting from condensation of the overhead product from the first distillation zone can be separated from a gas stream containing any hydrogen, which was dissolved in the crude reaction product, and the gas stream can then be purged from the process. This purge gas can be burnt as fuel in the process or passed to a flare stack. In this way formation of potentially explosive mixtures of air and hydrogen, such as might be formed in a tetrahydrofuran recovery plant of the type described in EP-A-0255400 is avoided.

Hence, the invention further provides, in a preferred aspect thereof, a process for the separation of tetrahydrofuran in a distillation plant from a crude reaction product containing, in addition to tetrahydrofuran, also dissolved hydrogen, ethanol, water, and n-butanol, and significant amounts of high boiling materials including butane-1,4-diol and gamma-butyrolactone, which process comprises:

(i) supplying the crude reaction product to a first distillation zone which is operated substantially at atmospheric pressure;
(ii) recovering a vaporous first overhead product from the first distillation zone containing hydrogen, tetrahydrofuran, ethanol and water;
(iii) cooling said vaporous first overhead product to effect separation by condensation of a first condensate from a gaseous stream containing hydrogen, said first condensate containing tetrahydrofuran, ethanol and water;
(iv) purging the gaseous stream of step (iii) from the distillation plant;
(v) redistilling the first condensate in a second distillation zone which is operated substantially at atmospheric pressure;
(vi) supplying to an upper part of the second distillation zone a hydroxylic solvent containing at least two hydroxyl groups;
(vii) recovering a second overhead product from the second distillation zone consisting essentially of tetrahydrofuran;
(viii) condensing said second overhead product;
(ix) recovering a bottom product from a lower part of the second distillation zone comprising hydroxylic solvent, tetrahydrofuran, ethanol and water;
(x) stripping tetrahydrofuran, ethanol and water from the bottom product of step (ix) by distillation in a third distillation zone; and
(xi) recycling stripped bottom product of step (x) to the second distillation zone.

As examples of hydroxylic solvents containing at least two hydroxyl groups there can be mentioned butane-1,4-diol, glycerol, diethylene glycol, butane-1,2-diol, triethylene glycol and the like. Preferably the hydroxylic solvent has a boiling point at atmospheric pressure of at least about 200° C. and preferably at least about 230° C.

In the process of the invention the hydroxylic solvent is preferably supplied to the second distillation zone in an amount sufficient to provide a molar ratio of hydroxylic solvent:tetrahydrofuran in the second distillation zone of from about 3:1 to about 10:1.

The material which is stripped in step (g) from the bottom product from the second distillation zone is conveniently returned to the first distillation zone.

The bottom product from the first distillation zone in the process of the invention contains, in addition to butane-1,4-diol and gamma-butyrolactone, also water, ethanol, n-butanol and any other minor constituents present in the crude hydrogenation product, such as diethyl succinate and a minor amount of diethyl ethoxysuccinate. This bottom product from the first distillation zone is conveniently passed to a fourth distillation zone, which can also be operated at atmospheric pressure but is preferably operated under vacuum (e.g. at a pressure of from about 0.01 bar up to about 0.7 bar) so as to strip any remaining "light ends" from the bottom product. From this fourth distillation zone is recovered overhead a vaporous mixture containing water, ethanol and n-butanol. This mixture can then be redistilled in a further distillation column to give, as overhead product, a water/ethanol azeotrope and, as bottom product, substantially pure n-butanol.

In the process of the invention the hydroxylic solvent is circulated in a loop between the second and third distillation zones. Provision may be made for supplying to this loop any necessary make up hydroxylic solvent and for taking a purge therefrom as may be necessary.

In order that the invention may be clearly understood and readily carried into effect a preferred process for the continuous production of tetrahydrofuran in accordance with the invention and a plant designed for operation thereof will now be described, by way of example only, with reference to the accompanying drawing.

BRIEF DESCRIPTION OF THE DRAWINGS

The drawing is a schematic flow diagram of a plant for producing tetrahydrofuran.

It will be understood by those skilled in the art that, as the drawing is diagrammatic, further items of equipment such as condensers, heat exchangers, reflux drums, column reboilers, pumps, vacuum pumps, temperature sensors, pressure sensors, pressure relief valves, control valves, flow controllers, level controllers, holding tanks, storage tanks, and the like, would additionally be required in a commercial plant. The provision of such additional items of equipment forms no part of the present invention and is in accordance with conventional chemical engineering practice.

Referring to the drawing, maleic anhydride is supplied in line 1 to an esterification plant 2 which is also supplied in line 3 with ethanol. Esterification plant 2 produces a stream of acid-free diethyl maleate in line 4, part of which is fed by way of lines 5, 6 and 7 to a vapor phase catalytic hydrogenation plant 8 which is also fed with hydrogen in line 9. In plant 8 the diethyl maleate is hydrogenated in the presence of excess gaseous hydrogen by passage, in the vapor phase, over a copper chromite catalyst to produce a crude product stream in line 10 that is substantially free from diethyl maleate and contains, as products, a mixture of butane-1,4-diol, gamma-butyrolactone, and tetrahydrofuran, and, as recyclable materials, diethyl succinate, and ethanol, as well as minor amounts of by-products, including water, n-butanol, and "heavies" such as diethyl ethoxysuccinate.

Esterification plant 2 may include a non-catalytic monoesterification stage, in which maleic anhydride is reacted with excess ethanol to yield monoethyl maleate according to the following equation:

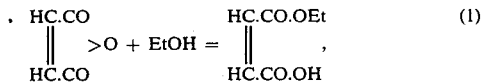
(1)

and one or more catalytic esterification stages, in which the resulting monoethyl maleate is further reacted with ethanol to yield diethyl maleate, according to the following equation:

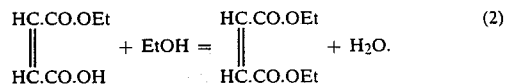
(2)

Although homogeneous liquid phase esterification catalysts, such as sulphuric acid, can be used, it is preferred to use in the catalytic esterification stage or stages a heterogeneous solid catalyst, such as an ion exchange resin containing sulphonic acid groups, for example Amberlyst 16. (The word "Amberlyst" is a trade mark). This obviates the need to neutralise the catalyst as is necessary when using a homogeneous catalyst, such as sulphuric acid. Hence the production of significant quantities of waste liquors and loss of potential product, in the form of monoethyl maleate, therein is avoided by use of a heterogeneous catalyst. Since equation (2) is reversible, as much water of esterification as possible must be removed if the yield of diethyl maleate is to be maximised.

In one scheme monoethyl maleate is passed in co-current with excess ethanol through a primary esterification reactor containing a charge of a suitable ion exchange resin (e.g. Amberlyst 16), the resulting intermediate reaction mixture is distilled to remove excess ethanol and water therefrom, and then the bottom product containing a mixture of mono- and diethyl maleates is fed in countercurrent to dry ethanol through one or more further esterification stages, each also containing a charge of a resin catalyst (e.g. Amberlyst 16). Further details of such a plant can be found in EP-A-0255399.

Final traces of monoethyl maleate and any other acid material present can be removed from the system by a two stage distillation procedure according to the teachings of EP-A-0255401, possibly followed by the washing procedure taught in GB-A-2193207. In this two stage distillation procedure monoethyl maleate is allowed to decompose thermally in the first distillation stage to yield ethanol, which is removed overhead, and maleic anhydride, which co-distils with product diethyl maleate and is separated therefrom in a second distillation stage. Further distillation stages can be used to remove the final traces of acid materials therefrom. The alternative washing procedure involves washing the ester with an alkaline solution of disodium maleate containing an alkali metal hydroxide, carbonate, bicarbonate or a mixture thereof, following by distillation, to remove traces of water and sodium ions.

In an alternative esterification process described in WO-A-88/00937, a primary esterification reactor is used that contains a charge of Amberlyst 16 resin, or similar solid catalyst. The resulting mixture of diethyl maleate, monoethyl maleate, ethanol and water is distilled to remove substantially all the ethanol and water therefrom, and the ester mixture (typically containing an approximately 65:35 molar mixture of diethyl and monoethyl maleates) is reacted with further ethanol in a continuously stirred tank reactor containing also a charge of Amberlyst 16 resin or other solid catalyst from which a stream containing an approximately 85:15 molar mixture of diethyl and monoethyl maleates, water and ethanol is recovered. This is then distilled to remove substantially all water and ethanol therefrom and the residue is subjected to the procedure of EP-A-0255401 and possibly also to the procedure of GB-A-2193207.

Hydrogenation plant 8 may include a single catalytic zone or may include two hydrogenolysis zones operated according to the teachings of EP-A-0143634, of WO-A-86/03189 or of WO-A-86/07358.

The crude hydrogenation product is fed by way of lines 10 and 11 to a first distillation column 12 which is operated at a pressure of 1.1 bar and at a head temperature of 66.1° C. A mixture of tetrahydrofuran, ethanol and water is recovered overhead in line 13, together with any hydrogen dissolved in the crude product in line 10. This mixture is condensed by cooling in a condenser 13C before being passed in line 14 to a second distillation column 15. A vent gas stream consisting mainly of hydrogen is taken in line 16 for use as a fuel or for venting to a flare stack. Column 15 is operated at 1.1 bar and with a head temperature of 68.3° C. A stream of butane-1,4-diol is fed to an upper part of second distillation column 15 in line 17 at a mass flow rate which is approximately 6 to 7 times that of the mass flow rate in line 14 so as to give a butane-1,4-diol:tetrahydrofuran molar ratio of approximately 4.5:1 in second distillation column 15. Essentially pure tetrahydrofuran is recovered as an overhead product from second distillation column 15 in line 18. The tetrahydrofuran product is condensed in condenser 18C.

The bottom product in line 19 from second distillation column 15 is a wet mixture of tetrahydrofuran, ethanol, and a minor amount of n-butanol, dissolved in butane-1,4-diol. This is passed to a third distillation column 20 in which tetrahydrofuran, ethanol, and any n-butanol are stripped from it and appear overhead in line 21. The mixture in line 21 is admixed with recycled material in line 22 and returned to first distillation column 12 by way of lines 23 and 11. The stripped butane-1,4-diol is recycled to the second distillation column 15 by way of lines 24, 25 and 17. A purge stream can be taken in line 26 and any make up butane-1,4-diol required to sustain the circulating flow of butane-1,4-diol between second and third distillation columns 22 can be supplied in line 27 from the downstream part of the plant, which is described further below.

The bottom fraction from first distillation column 12 contains, in addition to the high boiling materials present, such as butane-1,4-diol, gamma-butyrolactone, diethyl succinate, and a minor amount of diethyl ethoxysuccinate and other "heavies", also ethanol, water, and n-butanol, but only a trace amount of tetrahydrofuran. This bottom fraction is passed in line 28 to a fourth distillation column 29 which is operated at a pressure of 0.26 bar. Low boiling materials, i.e. remaining traces of tetrahydrofuran, water, ethanol and n-butanol are recovered overhead in line 30 at a head temperature of 47.8° C. and are mixed with make-up ethanol supplied in line 31. The resulting mixed stream is supplied in line 32 to a fifth distillation column 33. Column 33 is operated at 2 bar and at a head temperature of 96.7° C. A wet ethanol stream is recovered overhead in line 3 for use in the esterification plant 2. Esterification plant 2 includes a water recovery section (not shown) whereby the water mass balance of the plant can be maintained.

The bottom product from fifth distillation column 33, which is recovered in line 34, is substantially pure n-butanol.

The "heavy ends" fraction in line 35 from fourth distillation column 29 is a mixture containing, in addition to butane-1,4-diol and gamma-butyrolactone, a minor amount of diethyl succinate, as well as a minor amount of "heavies", such as diethyl ethoxysuccinate. This is fed to a sixth distillation column 36 which is operated under vacuum at a pressure of 0.13 bar with a head temperature of 136° C. The overhead product from column 36 is a mixture of diethyl succinate, gamma-butyrolactone and a minor amount of butane-1,4-diol; this is passed by way of lines 37 and 38 to a seventh distillation column 39 which is operated at a pressure of 0.13 bar and at a head temperature of approximately 141° C. Column 39 is also supplied by way of line 40, at a point above the point of connection of line 38, with diethyl maleate from line 4 via line 41. Hence the mixture of gamma-butyrolactone, diethyl succinate and butane-1,4-diol in line 38 is distilled in seventh column 39 in the presence of diethyl maleate. The overhead product in line 42 from column 39 is a mixture of diethyl maleate and gamma-butyrolactone. The bottom product from column 39 comprises a mixture of diethyl succinate and diethyl maleate, and possibly a trace amount of "heavies"; this is taken by way of line 43 and admixed with diethyl maleate in line 5 to form the stream in line 6. Hence the diethyl succinate and diethyl maleate recovered from the bottom of column 39 are recycled to the hydrogenation plant 8 by way of lines 6 and 7.

If desired some of the material in line 37 can be recycled to the hydrogenation plant by way of lines 44 and 7.

As already mentioned, the stream in line 42 is substantially free from diethyl succinate and consists predominantly of a mixture of gamma-butyrolactone and diethyl maleate. This is passed to an eighth distillation column 45 which is operated at a pressure of 0.13 bar and at a head temperature of 135° C. A side stream is taken from near the top of column 45 in line 46. This stream consists essentially of gamma-butyrolactone. A purge stream can be taken in line 47 for recycle of any "lights" which reach column 45 to first distillation column 12; this purge stream is recycled from line 47 by way of lines 22, 23 and 11.

The bottom product from column 45 is mainly diethyl maleate but contains also a minor amount of gamma-butyrolactone. This is recycled to seventh distillation column 39 by way of lines 49 and 40.

Although columns 39 and 45 could be combined into a single column, it is preferred to utilise two columns 39 and 45 so as to reduce the danger of carryover of diethyl succinate. Thus, if for any reason, the output from esterification plant 2 should be interrupted so that no diethyl maleate is temporarily available in line 4 for supply to line 41, then diethyl maleate can be recycled between columns 39 and 45 by way of lines 49 and 40, thus ensuring that diethyl succinate appears in the bottom product in line 43 from column 39 and not in the gamma-butyrolactone product in line 46, until either columns 39 and 45 can be shut down or else the supply of diethyl maleate in line 4 can be restored.

As described above, part of the diethyl maleate in line 4 of the plant of the drawing flows to hydrogenation plant 8 in lines 5, 6 and 7, whilst the remainder flows in lines 41 and 40 to column 39. If desired, or if more convenient or expedient, line 5 can be omitted so that all of the diethyl maleate from line 4 passes by way of lines 41 and 40 to column 39 and thence by way of lines 43, 6 and 7 to the hydrogenation plant 8.

Reverting to sixth column 36, the bottom product therefrom in line 50 is a mixture of butane-1,4-diol and "heavies". This is distilled in ninth distillation column 51 which is operated at a pressure of 0.1 bar and at a head temperature of 162.2° C. A stream of substantially pure butane-1,4-diol is recovered from near the top of column 51 in line 52. Part of this can be used to supply make up butane-1,4-diol to second distillation column 15 in line 27, whilst the remainder is passed on as product butane-1,4-diol in line 53. A bleed stream may be taken from the reflux stream for column 51 in line 54 and recycled to first distillation column 12 by way of lines 55, 22, 23 and 11 for the purpose of recycling any "lights" which may reach column 51.

The bottom product from distillation column 51 contains butane-1,4-diol and "heavies", such as diethyl ethoxysuccinate. This stream in line 56 is passed to a tenth distillation column 57 which is operated at a head temperature of 165° C. and at a pressure of 0.1 bar. The overhead product in line 58 is combined with overhead product in line 54 and passed by way of lines 55, 22, 23 and 11 to first distillation column 12. A bottom product stream consisting mainly of diethyl ethoxysuccinate and other "heavies" in line 59 can be exported beyond site limits or can be used as boiler fuel in the plant.

In the plant of the drawing distillation columns 39 and 45 are operated according to the teachings of EP-A-0255400. Instead of supplying diethyl maleate to column 39 in line 40 it is alternatively possible to omit line 41 and to supply in line 40 to column 39 another ester, such as diethyl ethoxysuccinate, as taught by copending U.S. Patent Application No. 07/223,079, filed July 22, 1988, or di-n-butyl maleate, as taught by copending U.S. Patent Application No. 07/222,728, filed July 22, 1988, now abandoned. In this case the bottom products from columns 39 and 45 should be distilled to separate the more volatile materials present, such as gamma-butyrolactone, from the ester supplied by way of line 40. That ester can then be recycled to column 39, after addition of any necessary make-up ester, while the more volatile products are recycled to hydrogenation plant 8 by way of lines 6 and 7. If diethyl ethoxysuccinate is used then, as this is a minor by-product of the hydrogenation step effected in hydrogenation plant 8, a suitable make-up supply of diethyl ethoxysuccinate can be obtained by distillation of the stream in line 52.

The invention is further illustrated in the following Example.

EXAMPLE

Distillation of a crude product obtained by vapor phase hydrogenation of diethyl maleate according to the teachings of EP-A-0143634 was effected on a pilot plant scale using a 12.2 m (40 feet) distillation column with an internal diameter of 0.1 m (4 inches) made of 316 stainless steel packed with six beds of Sulzer Mellapak 500Y stainless steel packing. (The word "Mellapak" is a trade mark).

The column was provided with an oil heated reboiler. Each section of the column corresponding to a particular bed was lagged and could be electrically heated to enable adiabatic conditions to be maintained in the column. A liquid distributor/re-distributor and a vapor distributor were positioned between each adjacent pair of beds within the column.

The crude product was supplied continuously to the column above the third bed of packing from the bottom at a feed temperature of 70° C. using a column top pressure of 1.03 bar (770 mm Hg). The column head temperature was 65.8° C. and the reflux ratio was 20:1. 762.39 kg of crude product was fed to the distillation column; 50.80 kg of overhead product was recovered from the top of the column as a condensate and 709.48 kg of bottoms product was recovered from the sump of the column, corresponding to a weight balance of 99.7% in this first distillation step. (The small apparent loss can be attributed to experimental error). The mol % composition of the various streams was as set out below in Table I.

TABLE I

| Component | Feed | Overhead | Bottoms |
| --- | --- | --- | --- |
| Tetrahydrofuran | 4.82 | 80.64 | 0.04 |
| Ethanol | 59.08 | 5.11 | 63.10 |
| Water | 9.52 | 14.17 | 9.10 |
| n-butanol | 0.17 | 0 | 0.19 |
| gamma-butyrolactone | 10.27 | 0 | 11.00 |
| butane-1,4-diol | 14.71 | 0 | 15.07 |

TABLE I-continued

| Component | Feed | Overhead | Bottoms |
| --- | --- | --- | --- |
| diethyl succinate | 1.22 | 0 | 1.27 |
| "unknown(s)" | 0.21 | 0.08 | 0.23 |

The overhead product from this first distillation step was re-distilled in the same column at 1.03 bar (770 mm Hg), being continuously supplied as feed above the first bed of packing from the bottom of the column at 18° C. Butane-1,4-diol was supplied to the top of the column at a feed temperature of 61° C. An overhead vaporous product was recovered from the top of the column and condensed. A bottom product was taken from the sump of the column. The weight ratio of feed:butane-1,4-diol was 0.21:1. The compositions of the various stream in mol % were as set out in Table II below.

TABLE II

| Component | Butane-1,4-diol | Overhead | Bottoms |
| --- | --- | --- | --- |
| Tetrahydrofuran | 0 | 96.37 | 5.69 |
| Ethanol | 0 | 0.21 | 2.60 |
| Water | 0.48 | 3.10 | 2.82 |
| gamma-butyrolactone | 0 | 0 | 0 |
| Butane-1,4-diol | 99.21 | 0.21 | 88.66 |
| "Unknown(s)" | 0.31 | 0.11 | 0.23 |

614.3 kg of butane-1,4-diol was supplied to the column in this second distillation step whilst 114.0 kg of feed material was fed to the column above the first bed of packing. 65.8 kg of condensate comprising essentially pure tetrahydrofuran was recovered overhead from the column, as well as 662.5 kg of bottoms product. The mass balance was calculated to be 100%.

The bottoms product from the first distillation step was re-distilled in the same column at a pressure of 0.26 bar (197 mm Hg) and at a head temperature of 44° C. The feed was continuously supplied, above the second bed of packing from the bottom of the column, at a temperature of 82.2° C. under a reflux ratio of 0.35:1. 705.75 kg of feed yielded 379.01 kg of overhead condensate and 324.57 kg of bottoms product, corresponding to a weight balance of 99.7% (the balance being attributable to experimental error). The compositions in mol % of the streams were as set out in Table III.

TABLE III

| Component | Overhead | Bottoms |
| --- | --- | --- |
| Tetrahydrofuran | 0.02 | 0.09 |
| Ethanol | 87.17 | 0.20 |
| Water | 12.55 | 0.06 |
| n-butanol | 0.23 | Trace |
| gamma-butyrolactone | — | 39.68 |
| Butane-1,4-diol | — | 54.90 |
| Diethyl succinate | — | 4.27 |
| "Unknown(s)" | 0.03 | 0.80 |

What is claimed is:

1. A continuous process for the separation of tetrahydrofuran from a crude reaction product containing, in addition to tetrahydrofuran, ethanol, water, and n-butanol, and high boiling materials including butane-1,4-diol and gamma-butyrolactone, which process comprises:
   (a) supplying the crude reaction product to a first distillation zone;
   (b) recovering a vaporous first overhead product from the first distillation zone containing tetrahydrofuran, ethanol and water;

(c) redistilling the overhead product from the first distillation zone in a second distillation zone;

(d) supplying to an upper part of the second distillation zone a hydroxylic solvent containing at least two hydroxyl groups;

(e) recovering an overhead product from the second distillation zone consisting essentially of tetrahydrofuran;

(f) recovering a bottom product from a lower part of the second distillation zone comprising hydroxylic solvent, tetrahydrofuran, ethanol and water;

(g) stripping tetrahydrofuran, ethanol and water from the bottom product of step (f) by distillation in a third distillation zone; and (h) recycling stripped bottom product of step (g) to the second distillation zone.

2. A process according to claim 1, in which the first distillation zone is operated substantially at atmospheric pressure.

3. A process according to claim 1, in which the second distillation zone is operated substantially at atmospheric pressure.

4. A process according to claim 1, in which the overhead product from the first distillation zone is condensed prior to entry to the second distillation zone.

5. A process according to claim 4, in which the condensate resulting from condensation of the overhead product from the first distillation zone is separated from a gas stream containing hydrogen dissolved in the crude reaction product and in which the gas stream is purged from the process.

6. A process according to claim 1, in which a bottom product containing, in addition to high boiling materials including butane-1,4-diol and gamma-butyrolactone, ethanol, n-butanol and water is recovered from the first distillation zone and is redistilled in a fourth distillation zone to produce an overhead product containing ethanol, water and n-butanol and a bottom product containing said high boiling materials.

7. A process according to claim 6, in which the fourth distillation zone is operated under vacuum.

8. A process according to claim 6, in which the overhead product from the fourth distillation zone is redistilled in a fifth distillation zone to separate a water and ethanol mixture as overhead product from a bottom product consisting essentially of n-butanol.

9. A process according to claim 1, in which the hydroxylic solvent has a boiling point at atmospheric pressure of at least about 200° C.

10. A process according to claim 9, in which the hydroxylic solvent is selected from a group consisting of butane-1,4-diol, glycerol, diethylene glycol, butane-1,2-diol, and triethylene glycol.

11. A process according to claim 1, in which tetrahydrofuran, ethanol and water stripped in step (g) from the bottom product of step (f) are recycled to the first distillation zone.

12. A continuous process for the separation of tetrahydrofuran in a distillation plant from a crude reaction product containing, in addition to tetrahydrofuran, dissolved hydrogen, ethanol, water and n-butanol, and high boiling materials including butane-1,4-diol and gamma-butyrolactone, which process comprises:

(i) supplying the crude reaction product to a first distillation zone which is operated substantially at atmospheric pressure;

(ii) recovering a vaporous first overhead product from the first distillation zone containing hydrogen, tetrahydrofuran, ethanol and water;

(iii) cooling said vaporous first overhead product to effect separation by condensation of a first condensate from a gaseous stream containing hydrogen, said first condensate containing tetrahydrofuran, ethanol and water;

(iv) purging the gaseous stream of step (iii) from the distillation plant;

(v) redistilling the first condensate in a second distillation zone which is operated substantially at atmospheric pressure;

(vi) supplying to an upper part of the second distillation zone a hydroxylic solvent containing at least two hydroxyl groups;

(vii) recovering a second overhead product from the second distillation zone consisting essentially of tetrahydrofuran;

(viii) condensing said second overhead product;

(ix) recovering a bottom product from a lower part of the second distillation zone comprising hydroxylic solvent, tetrahydrofuran, ethanol and water;

(x) stripping tetrahydrofuran, ethanol and water from the bottom product of step (ix) by distillation in a third distillation zone; and (xi) recycling stripped bottom product of step (x) to the second distillation zone.

13. A process according to claim 12, in which a bottom product containing, in addition to high boiling materials including butane-1,4-diol and gamma-butyrolactone, ethanol, n-butanol and water is recovered from the first distillation zone and is redistilled in a fourth distillation zone to produce an overhead product containing ethanol, water and n-butanol and a bottom product containing said high boiling materials.

14. A process according to claim 13, in which the fourth distillation zone is operated under vacuum.

15. A process according to claim 13, in which the overhead product from the fourth distillation zone is redistilled in a fifth distillation zone to separate a water and ethanol mixture as overhead product from a bottom product consisting essentially of n-butanol.

16. A process according to claim 12, in which the hydroxylic solvent has a boiling point at atmospheric pressure of at least about 200° C.

17. A process according to claim 16, in which the hydroxylic solvent is selected from a group consisting of butane-1,4-diol, glycerol, diethylene glycol, butane-1,2-diol, and triethylene glycol.

18. A process according to claim 12, in which tetrahydrofuran, ethanol and water stripped in step (x) from the bottom product of step (ix) are recycled to the first distillation zone.

* * * * *